US006253766B1

(12) United States Patent
Niles et al.

(10) Patent No.: US 6,253,766 B1
(45) Date of Patent: Jul. 3, 2001

(54) CONTINUOUS POSITIVE AIRWAY PRESSURE THERAPY DEVICE

(75) Inventors: Rex A. Niles; Lawrence A. Weinstein, both of Oneida; Stephen D. Diehl, Waterville, all of NY (US)

(73) Assignee: DHD Healthcare Corporation, Canastota, NY (US)

( * ) Notice: Subject to any disclaimer, the term of this patent is extended or adjusted under 35 U.S.C. 154(b) by 0 days.

(21) Appl. No.: 09/382,063

(22) Filed: Aug. 24, 1999

(51) Int. Cl.[7] .................................................. A61M 16/00
(52) U.S. Cl. ................................. 128/204.24; 128/204.25
(58) Field of Search ........................ 128/204.24, 204.25, 128/DIG. 10; 137/888

(56) References Cited

U.S. PATENT DOCUMENTS 4,261,355    4/1981    Glazener .

OTHER PUBLICATIONS

Exair—Amplifiers, Exair Corp.
Infant Flow System Coanda Effect, E.M.E. Electro Medical Equipment.
Aladdin Infant Flow System, Hamilton Medical.
C.P.A.P. "T", E.L. Glazener.
Evaluation & Clinical Application of a New CPAP Device, Apr. 28, 1980, ASA Abstracts.
Equipment A New Continuous Positive Airway Pressure (CPAP) Device by K. Hillman & C. Huggins, May 1991, Anesthesia & Intensive Care, vol. 19, No. 2.
Tests of Six Continuous Flow CPAP Devices by Y. Shehabi et al. May 1991, Anesthesia & Intensive Care, vol. 19, No. 2.
Description & clinical evaluation of a new continuous positive airway pressure device by Barry G. Zamost et al. Feb. 1981, Critical Care Medicine vol. 9, No. 2.

Primary Examiner—John G. Weiss
Assistant Examiner—Mital Patel
(74) Attorney, Agent, or Firm—August E. Roehrig, Jr.; Hancock & Estabrook, LLP

(57) ABSTRACT

An improved continuous positive airway pressure therapy device including a ring orifice through which compressed air or oxygen is introduced to effectively amplify the air flow to the patient by drawing ambient air into the device inlet for maintaining a continuous positive pressure of a patient's lungs during all portions of the breathing cycle.

12 Claims, 6 Drawing Sheets

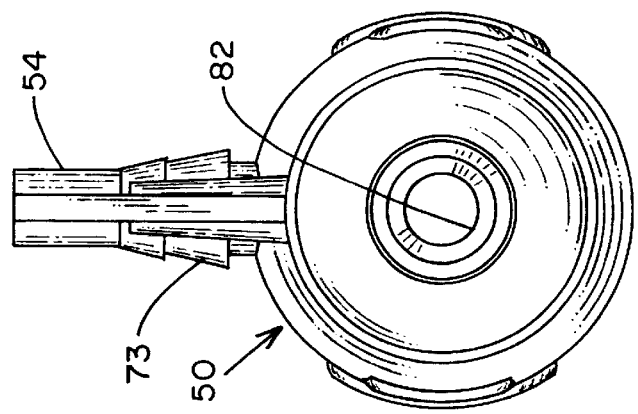
FIG. 4
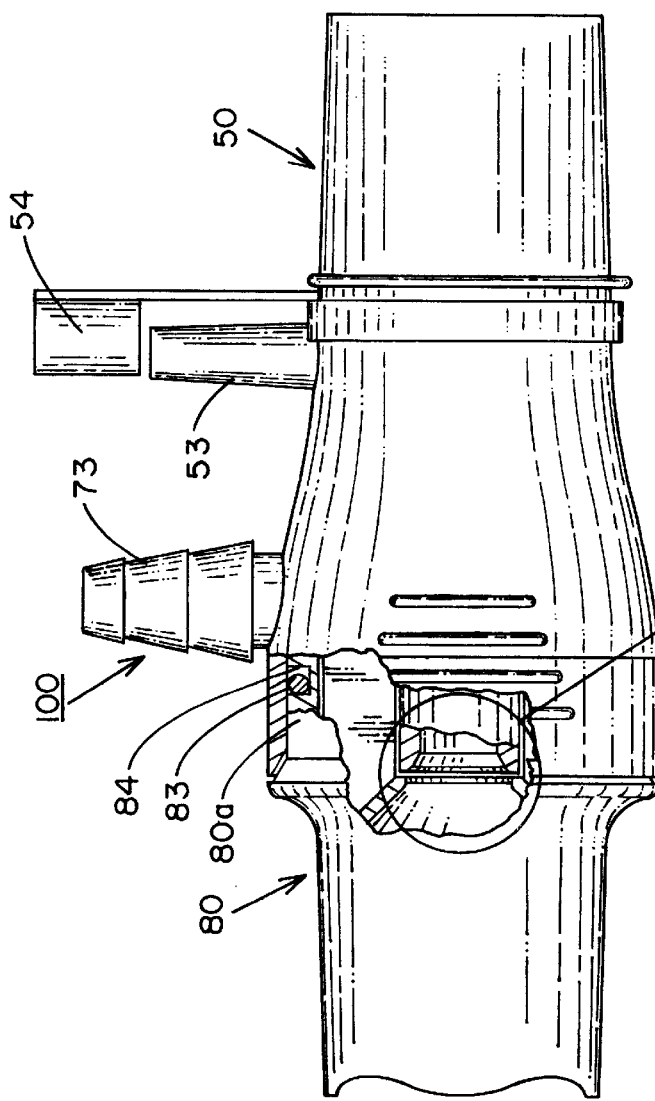
FIG. 3
FIG. 3a

CONTINUOUS POSITIVE AIRWAY PRESSURE THERAPY DEVICE

BACKGROUND OF THE INVENTION

1. Field of the Invention

This invention relates in general to respiratory therapy devices and, in particular, to a continuous positive airway pressure therapy device which maintains continuous positive pressure to a patient's lungs through the use of a flow amplifier for maintaining the positive pressure during a patient's inspiration, breath pause and expiration portions of the breathing cycle.

More specifically, but without restriction to the particular embodiment and/or use which is shown and described herein for purposes of illustration, this invention relates to a continuous positive airway pressure therapy device having a flow amplifying body and which is adapted for connection to a source of compressed air or oxygen to generate a positive airway pressure during inhalation, breath pause and exhalation.

2. Description of Related Art

Devices for maintaining or inducing a constant positive pressure within the airway passages of a patient are generally incorporated into breathing machine systems such as an anesthesia machine or respirators. Accordingly, such equipment is complicated, moderately cumbersome and expensive. While continuous positive airway pressure has been utilized for many forms of respiratory therapy, such as the treatment of pulmonary edema (cardiogenic and noncardiogenic), acute hypoaxaemic respiratory failure, thoracic trauma, asthma, chronic obstructive airway disease, pneumonitides, atelectasis and sleep apnoea, the availability of a simple, inexpensive and reliable continuous flow device would increase the therapeutic modality of this form of therapy. It would, therefore, be desirable to have such a continuous positive airway pressure device which would be capable of delivering a positive pressure to a patient's respiratory system throughout the patient's inspiratory and expiratory cycle, while minimizing the work of breathing created by the device.

The present invention provides such a device with the use of a nominal compressed gas source by utilizing a Coanda profile and an internal orifice to create a high velocity turbulent flow from the compressed gas source that effectively entrains ambient air flowing towards the patient thereby creating a positive airway pressure. This positive airway pressure amplifies the flow of ambient air to a patient during inhalation, maintains the positive pressure during breath pause while the flow of compressed gas is no longer directed towards the patient, and, upon expiration, the compressed gas flow is overcome by the patient's expiratory air flow while still providing positive airway pressure.

SUMMARY OF THE INVENTION

It is an object of this invention to improve continuous positive airway pressure therapy devices.

Another object of this invention is to provide a single patient use continuous positive airway pressure therapy device.

Still another object of this invention is to provide a continuous positive airway pressure therapy device which utilizes a compressed gas to generate positive airway pressure during patient inhalation, breath pause and exhalation.

Yet another object of this invention is to provide a continuous positive airway pressure therapy device which generates a positive airway pressure during a patient's inhalation, breath pause and exhalation by introducing a compressed gas through a ring orifice which effectively amplifies gas/air flow by drawing ambient air into the device.

These and other objects are attained in accordance with the present invention wherein there is provided an improved continuous positive airway pressure therapy device including a ring orifice through which compressed air or oxygen is introduced to effectively amplify the air flow to the patient by drawing ambient air into the device inlet for maintaining a continuous positive pressure of a patient's lungs during all portions of the breathing cycle.

DESCRIPTION OF THE DRAWINGS

Further objects of this invention, together with additional features contributing thereto and advantages accruing therefrom, will be apparent from the following description of a preferred embodiment of the present invention which is shown in the accompanying drawings with like reference numerals indicating corresponding parts throughout and which is to be read in conjunction with the following drawings, wherein:

FIG. 3 is a side elevational view of the invention with portions broken away to better illustrate the structure for producing the Coanda effect;

FIG. 3a is an enlarged view of a portion of FIG. 3;

FIG. 4 is an end view of the device illustrated in FIG. 3, looking inwardly from the patient input portion of the device;

Figure 1:
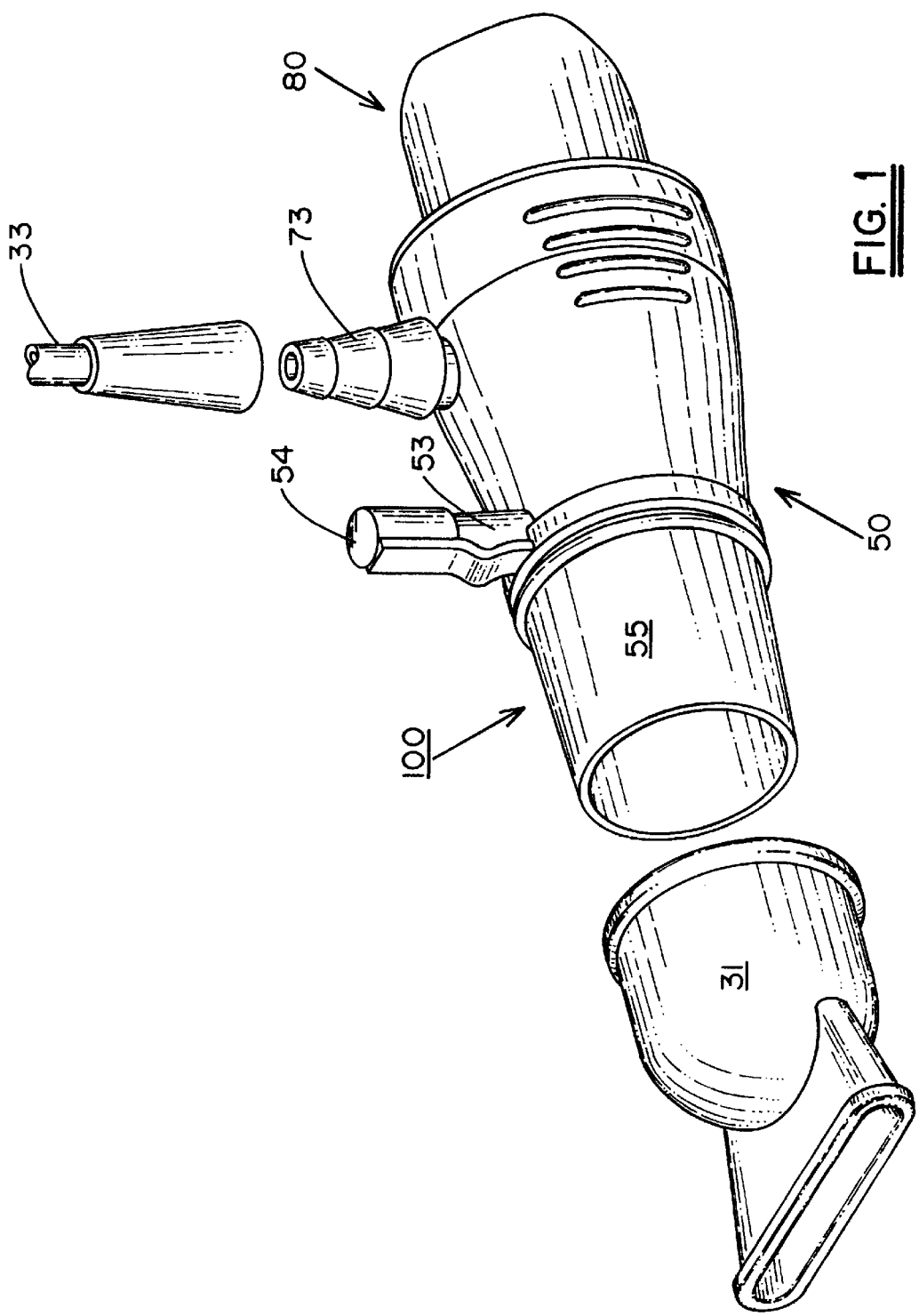
FIG. 1 is a frontal perspective view of the improved continuous positive airway pressure therapy device with a mouth piece and pressure hose which are attachable thereto.
Figure 2:
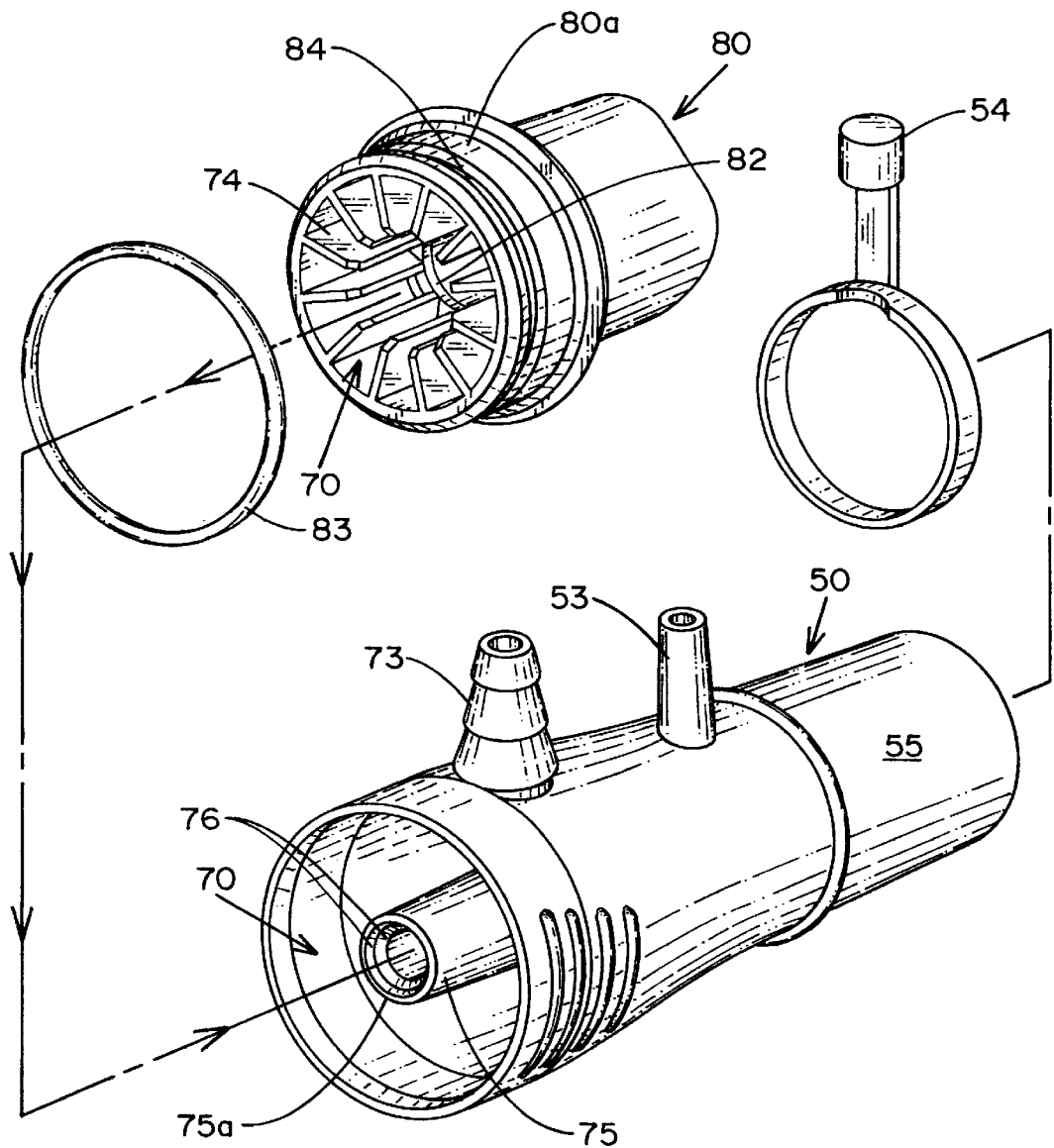
FIG. 2 is an exploded view of the continuous positive airway pressure therapy device to better illustrate the patient input and ambient air portions of the device and the components thereof.

This and additional embodiments of the invention may now be better understood by referring to the following detailed description of the invention wherein the illustrated embodiment is described.

DETAILED DESCRIPTION OF THE INVENTION

Throughout this description, the preferred embodiment and examples shown should be considered as exemplars, rather than limitations on the apparatus and methods of the present invention.

Referring now to the drawings, there is shown a continuous positive airway pressure therapy device (CPAP) 100 which includes a cylindrical patient input portion 50, through which a patient breathes, and a cylindrical ambient air portion 80, through which ambient inspiratory air passes when a patient inhales, and through which expiratory air is discharged when the patient exhales. A distal end 55 of the patient input portion 50 is sized to receive a standard 22 millimeter ID mouthpiece 31 or mask (not shown). An integral pressure port 53 is connected into the patient input portion 50 so that patient airway pressure can be monitored both during set up of the device 100 and during therapy. The pressure monitoring port 53 is adapted to be connected to standard flexible tubing (not shown) for connection to a pressure-monitoring device, such as an aneroid gauge. A pressure port cap 54 is attached to the patient input portion 50 so that the pressure port can be closed and the device 100 can be utilized without concurrent pressure monitoring. The pressure port 53 is formed at a position removed from an air flow amplifying chamber 70, to be hereinafter discussed in detail, so that the pressure reading taken therethrough will not be effected by the discharge of pressurized gas into the patient input portion 50 through a gas inlet port 73.

Figure 6:
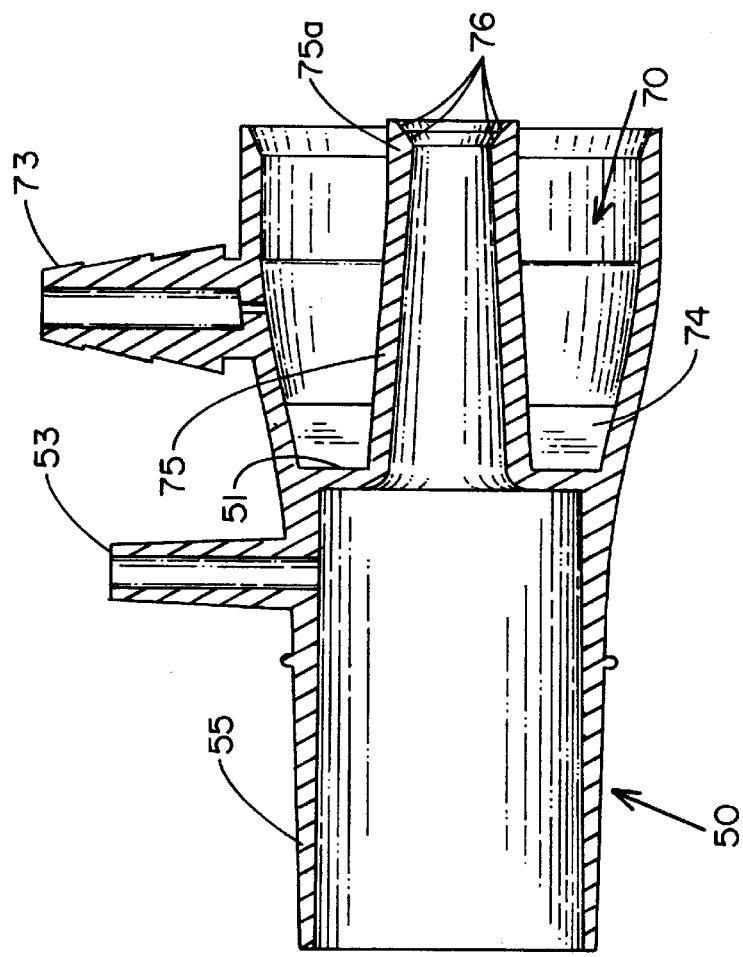
FIG. 6 is a cross sectional view of the patient input portion of the device illustrated in FIG. 3, taken in the direction of lines 6—6 of FIG. 5.
Figure 5:
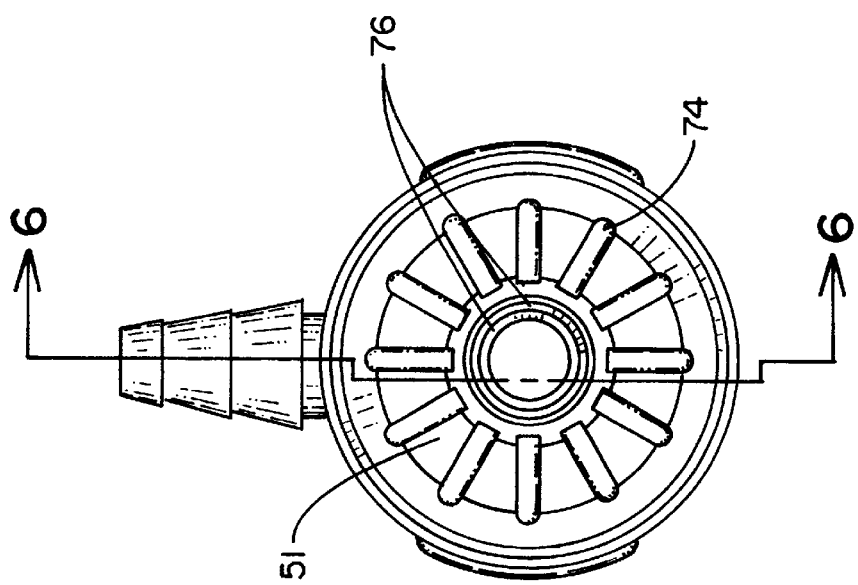
FIG. 5 is an end elevation view of the device illustrated in FIG. 3, looking inwardly from the ambient air portion of the device toward the patient input portion of the device.
Figure 8:
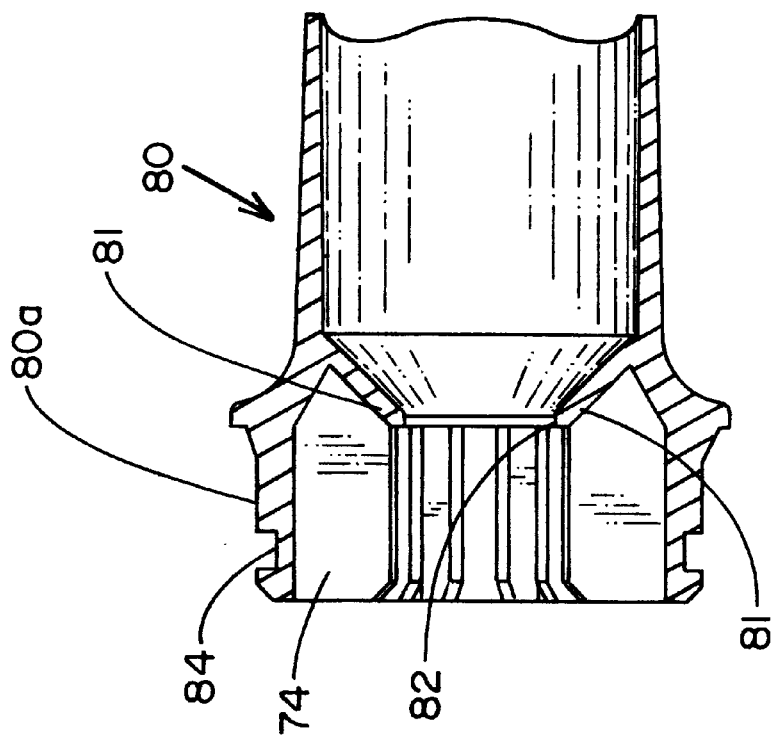
FIG. 8 is a cross sectional view of the ambient air portion of the device illustrated in FIG. 7, taken along lines 8—8.
Figure 7:
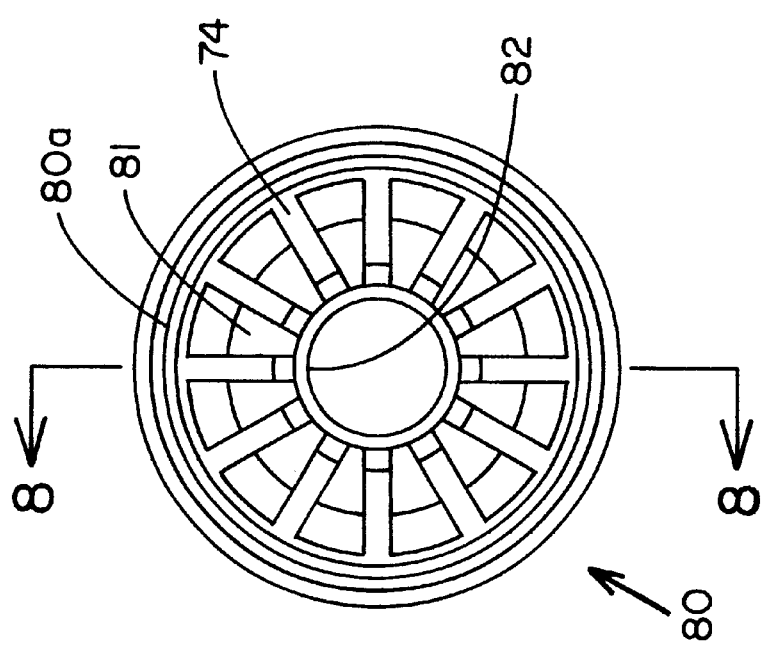
FIG. 7 is an end view of the ambient air portion of the device illustrated in FIG. 3 looking inwardly from the patient input portion.

As best shown in FIG. 1, a source of compressed air or oxygen is coupled to the CPAP through the gas inlet port 73, the interior of which is in fluid communication with the interior of the CPAP as shown in FIG. 6. The source of compressed air/oxygen is preferably supplied by an institutional air or oxygen source, such as in a hospital, connected to the gas input port 73 by means of a flexible tubing 33, of the type that may be connected to and controlled by means of a flow meter (not shown). However, it is to be understood that the source of compressed air or oxygen also could be supplied by a portable tank of such gas.

Pressurized gas is introduced through the pressure port 73 into an amplification chamber 70, a part of which is in each of the patient input portion 50 and the ambient air portion 80. The amplification chamber 70 is defined by an annular rear wall 51 within the patient input portion 50 of the CPAP 100, and a forward annular wall 81 within the ambient air portion 80. The forward annular wall 81 has an orifice 82 of a predetermined diameter formed therein for a purpose to be hereinafter described in detail. A part 80a of the ambient air portion 80 is insertable into the patient input portion 50, and to this end the outer surface of the insertable part 80a carries an "O" ring 83 positioned in a groove 84 on the exterior thereof to form a seal for sealing the insertable part 80a of the ambient air portion 80 with the patient input portion 50. A plurality of fins or vanes 74 are equally spaced about the interior circumference of the amplification chamber 70 adjacent to both the forward annular wall 81 and the rear annular wall 51. These vanes function to maintain proper alignment of a cylindrical conduit 75 with the orifice 82.

As best shown in FIG. 6, the cylindrical conduit 75 has a tapered open interior and extends forwardly from the rear wall 51 of the amplification chamber 70 to a position adjacent to and spaced from the orifice 82. In this manner, the amplification chamber 70 is sealed from the distal end 55 of the patient input portion except for the passage through the conduit 75. A free open end 75a of the conduit 75 extends forwardly to be received within the part of the amplification chamber 70 which is within the ambient air portion 80. The open end 75a of the conduit 75 extends outwardly from the rear wall 51 of the amplification chamber 70 a distance substantially equal to that of the outer cylindrical wall 50a of the patient input portion 50. Upon insertion of the part 80a of the ambient air portion 80 into the patient input portion 50, the end 75a will be positioned adjacent to the orifice 82 formed in the annular forward wall 81 of the amplification chamber 70. The positioning of the open free end 75a of the cylindrical conduit 75 adjacent to and spaced from the orifice 82 formed in the forward annular wall 81 forms an annular gap 85 therebetween through which pressurized air or other gas passing into the amplification chamber through the pressure port 73, is discharged. The gas passing through the annular gap 85 so created will flow toward the distal end 55 of the patient input portion 50 during patient inhalation, into both the patient input portion 50 and the ambient air portion 80 during breath pause, and into the ambient air portion 80 during a patient's exhalation, as will be explained with reference to FIGS. 9a, 9b and 9c.

The open forward end 75a of the cylindrical conduit 75 is formed with an inwardly stepped Coanda profile 76 which creates surface tension forces on the gas flowing thereover to divert the flow of the gas along the path of the tension force generating surfaces 76 in response to a patient's breathing cycle. This phenomenon of gas flow diversion is known as the Coanda effect. To create a Coanda effect, the free end 75a of the cylindrical conduit 75 is positioned a predetermined distance from the orifice, preferably between about 0.001"–0.005 and more particularly about 0.002", which has been found to produce the Coanda effect when gas is introduced at a rate of 5 to 15 LPM.

Figure 9A:
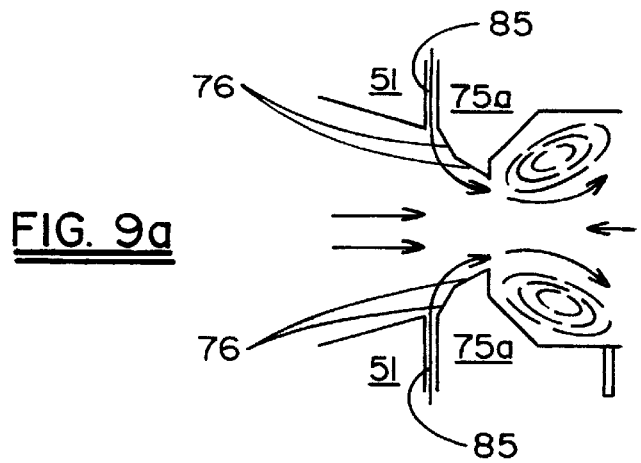
FIGS. 9a, 9b and 9c are diagrammatic representations of the air flow through the continuous positive airway pressure therapy device during a patient's inhalation of inspiratory air, pausing during the breath cycle, and exhalation of expiratory air, respectively.

To produce the Coanda effect, it has been found that the Coanda profile 76 may be created by forming inwardly stepped portions of the free end 75a of cylindrical conduit 75 with an angular relationship of about 25° and about 35° from the horizontal axis of the cylinder 75. When pressurized gas is introduced through the gas inlet port 73 at the preferred flow rate, the gas will flow across the Coanda profile 76 creating a high velocity, turbulent flow that effectively entrains ambient air being drawn into the CPAP by a patient, as illustrated in FIG. 9a, and direct the flow towards the distal end 55 of the device. During inhalation, positive air pressure is provided to the patient and the flow of ambient air towards the patient because of the Coanda effect generated by the Coanda profile 76, amplifies this flow to create a positive airway pressure.

Figure 9B:
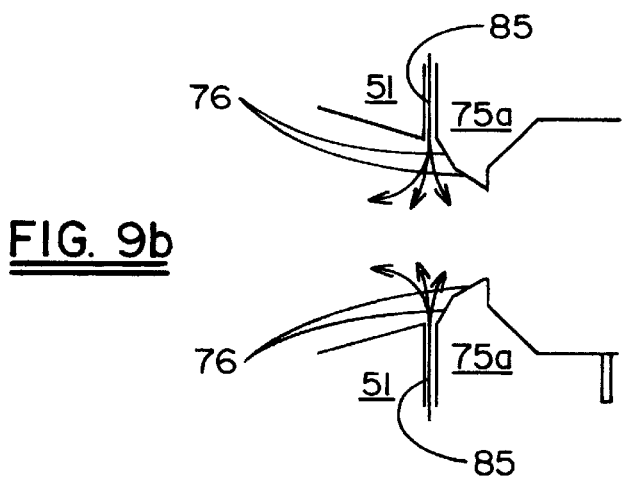

Referring to FIG. 9b, when a patient pauses during the breathing cycle, there will be no ambient air flow. Therefore, the pressurized gas passing through the annular orifice 85 will flow outwardly therefrom, no Coanda effect will occur, and a positive air pressure is maintained as the compressed gas flow bends back towards the ambient air portion 80 of the device.

Figure 9C:
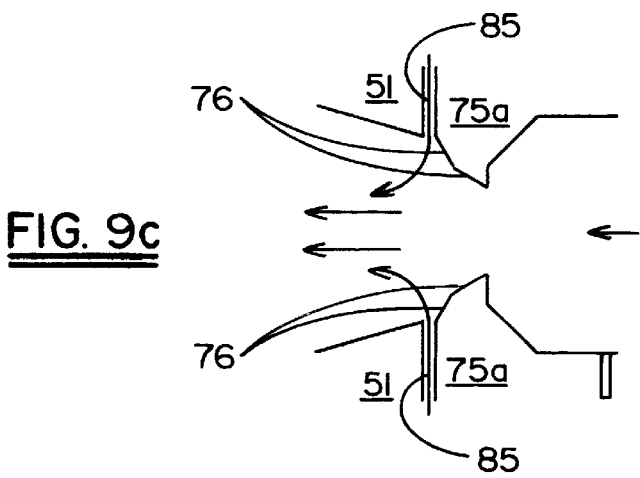

When the patient exhales, as illustrated in FIG. 9c, the discharge of the patient's expiratory air will overcome the force of the compressed gas flowing through the annular gap 85 across the Coanda profile 76 so that no Coanda effect occurs and the expiratory air will exit from the ambient air portion 80 of the device while providing positive air pressure against the patient's lungs.

While this invention has been described in the specification and illustrated in the drawings with reference to preferred embodiments, the structures of which have been disclosed herein, it will be understood by those skilled in the art to which this invention pertains that various changes maybe made, and equivalents maybe substituted for elements of the invention without departing from the scope of the claims. Therefore, it is intended that the invention not be limited to the particular embodiment disclosed in the specification and shown in the drawings as the best mode presently known by the inventors for carrying out this invention, nor confined to the details set forth, but that the invention will include all embodiments, modifications and changes as may come within the scope of the following claims.

It is claimed:

1. A respiratory therapy device for applying a continuous positive airway pressure to the respiratory system of a user during a breathing cycle of inhalation, pause and exhalation, comprising:

a housing having an opening therethrough through which a user may inhale inspiratory air into the user's respiratory system and exhale expiratory air from the user's respiratory system, said housing having a proximal end for engagement by a user and through which the user inhales and exhales, said housing having a distal end open to ambient air and through which user generated inspiratory air and expiratory air passes, an air flow amplification chamber within said housing positioned between said proximal end and said distal end of said housing for accelerating the flow of ambient air through said distal end during a user's inhalation of air through said proximal end of said housing, a gas port in fluid communication with said amplification chamber for coupling a source of pressurized gas through said housing into said amplification chamber, a conduit carried within said amplification chamber and communicating inspiratory air and expiratory air from said proximal end of said housing to said amplification chamber, said conduit having an open end thereof shaped in a Coanda profile for generating a Coanda effect on gas flowing thereover, and an orifice spaced a predetermined distance from said open end of said conduit for forming an annular opening about said conduit open end through which gas passing into said amplification chamber from said gas port flows to create a Coanda effect during a user's inhalation of ambient air producing a continuous positive airway pressure on the user's respiratory system during inhalation of ambient air.

2. The respiratory therapy device of claim 1 further including a pressure port in fluid communication with said proximal end of said housing for coupling the pressure within said proximal end of said housing to a pressure gauge.

3. The respiratory therapy device of claim 1 wherein said conduit carried within said amplification chamber is concentric with said housing.

4. The respiratory therapy device of claim 1 wherein pressurized gas is communicated to said amplification chamber through said gas port at a rate of about five to about fifteen liters per minute.

5. The respiratory therapy device of claim 1 wherein said Coanda profile formed on the open end of said conduit comprises inwardly stepped angular portions with an angular relationship of about 25° and about 35° from the horizontal axis of said conduit.

6. The respiratory therapy device of claim 2 further including a cover for selectively closing said pressure port.

7. The respiratory therapy device of claim 1 further including a mouth piece coupled to said proximal end of said housing.

8. A respiratory therapy device for applying a continuous positive airway pressure to the respiratory system of a user during a breathing cycle of inhalation, pause and exhalation, comprising:

a housing having an opening therethrough through which a user may inhale inspiratory air into the user's respiratory system and exhale expiratory air from the user's respiratory system, said housing having a proximal end for engagement by a user and through which the user inhales and exhales, said housing having a distal end open to ambient air and through which user generated inspiratory air and expiratory air passes, an air flow amplification chamber within said housing positioned between said proximal end and said distal end of said housing for accelerating the flow of ambient air through said distal end during a user's inhalation of air through said proximal end of said housing, said amplification chamber having a first end wall adjacent to said proximal end of said housing and a second end wall adjacent to said distal end of said housing, a gas port in fluid communication with said amplification chamber for coupling a source of pressurized gas through said housing into said amplification chamber, a conduit carried by said first end wall of said amplification chamber and communicating inspiratory air and expiratory air from said proximal end of said housing to said amplification chamber, said conduit having an open end thereof shaped in a Coanda profile for generating a Coanda effect on gas flowing thereover, and an orifice formed in said second end wall of said amplification chamber and spaced a predetermined distance from said open end of said conduit for forming an annular opening about said conduit open end through which gas passing into said amplification chamber from said gas port flows to create a Coanda effect during a user's inhalation of ambient air producing a continuous positive airway pressure on the user's respiratory system during inhalation of ambient air.

9. The respiratory therapy device of claim 8 wherein said conduit carried by said first end wall and said orifice formed in said second end wall are co-axial.

10. The respiratory therapy device of claim 9 wherein said conduit carried within said amplification chamber is concentric with said housing.

11. The respiratory therapy device of claim 10 wherein the open end of said conduit and the orifice formed in said second end wall are substantially the same diameter.

12. The respiratory therapy device of claim 11 wherein said Coanda profile formed on the open end of said conduit comprises inwardly stepped angular portions with an angular relationship of about 25° and about 35° from the horizontal axis of said conduit.

* * * * *